US012799506B2

(12) United States Patent
Kramer et al.

(10) Patent No.: US 12,799,506 B2
(45) Date of Patent: *Nov. 17, 2026

(54) PROCESSES AND SYSTEMS FOR BIOLOGICAL HYDROGEN PRODUCTION FROM ORGANIC WASTE USING YEAST

(71) Applicant: Purdue Research Foundation, West Lafayette, IN (US)

(72) Inventors: Robert A. Kramer, Crown Point, IN (US); Libbie S.W. Pelter, Schererville, IN (US); John A. Patterson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 310 days.

This patent is subject to a terminal disclaimer.

(21) Appl. No.: 18/504,690

(22) Filed: Nov. 8, 2023

(65) Prior Publication Data

US 2024/0132918 A1 Apr. 25, 2024

Related U.S. Application Data

(63) Continuation-in-part of application No. 17/763,761, filed as application No. PCT/US2020/052812 on Sep. 25, 2020, now Pat. No. 12,139,738.

(60) Provisional application No. 62/906,261, filed on Sep. 26, 2019.

(51) Int. Cl.

*C12P 3/00* (2006.01)
*C12N 1/165* (2026.01)
*C12R 1/865* (2006.01)

(52) U.S. Cl.

CPC ................ *C12P 3/00* (2013.01); *C12N 1/165* (2021.05); *C12R 2001/865* (2021.05)

(58) Field of Classification Search

CPC ..... C12P 3/00; C12N 1/165; C12R 2001/865; Y02E 50/30

See application file for complete search history.

(56) References Cited

U.S. PATENT DOCUMENTS

| | | | | |
|---|---|---|---|---|
| 10,202,622 | B2 | 2/2019 | Foody et al. | |
| 10,801,043 | B2 | 10/2020 | Pachapur et al. | |
| 2011/0207191 | A1 | 8/2011 | Um et al. | |
| 2014/0157777 | A1* | 6/2014 | Kramer et al. ........... | C12P 3/00 60/641.8 |
| 2022/0340937 | A1 | 10/2022 | Kramer et al. | |

FOREIGN PATENT DOCUMENTS

| | | |
|---|---|---|
| JP | 2022118282 | 8/2022 |

OTHER PUBLICATIONS

Battista et al., “Selection of the best pretreatment for hydrogen and bioethanol production from olive oil waste products”, Renewable Energy, 88 (2016), pp. 401-407. (Year: 2016).*

Cappai, G. et al., “An Experimental Study on Fermentative H2 Production from Food Waste as Affected by pH,” Waste Management, 34 (2014) pp. 1510-1519.

Cappelletti, B.M. et al., “Fermentative Production of Hydrogen from Cassava Processing Wastewater by Clostridium Acetobutylicum,” Renewable Energy, 36 (2011) pp. 3367-3372.

Goyal, Y. et al., “Metaabolic Engineering for Enhanced Hydrogen Production: A Review,” Can. J. Microbiol, 59 (2013) pp. 59-78.

Shi, Y. et al., “Hydrogen Bio-Production through Anaerobic Microorganism Fermentation Using Kitchen Wastes as Substrate,” Biotechnol Lett., 31, (2009), pp. 1327-1333.

Waks, Z. et al., “Engineering a Synthetic Dual-Organism System for Hydrogen Production,” Applied and Environmental Microbiology, (2009), pp. 1867-1875.

Wang, A-J. et al., “Biohydrogen Production from Anaerobic Fermentation,” Adv. Biochem Engin/Biotechnol (2012), pp. 143-163.

Wang, J. et al., “Clostridium Species for Fermentative Hydrogen Production: An Overview,” International Journal of Hydrogen Energy, 46 (2021) pp. 34599-34625).

Yasin, N.H.M. et al., “Microbial Characterization of Hydrogen-Producing Bacteria in Fermented Food Waste at Different pH Values,” International Journal of Hydrogen Energy 36 (2011), pp. 9571-9580.

Cappai, G., et al., “An Experimental Study on Fermentative H2 Production from Food Waste as Affected by pH,” Waste Management, 34, (2014), (10 pages).

Cappelletti, B., et al., “Fermentative Production of Hydrogen from Cassava Processing Wastewater by Clostridium Acetobutylicum,” Renewable Energy, 36, (2011), (6 pages).

Goyal, Y., et al., “Metabolic Engineering for Enhanced Hydrogen Production: A Review,” Can. J. Microbiol.,59, (Nov. 26, 2012 ), (21 pages).

International Search Report & Written Opinion for International Application No. PCT/US2023/037061, dated Aug. 2, 2024, (9 pages).

Shi, Y., et al., “Hydrogen Bio-Production Through Anaerobic Microorganism Fermentation Using Kitchen Wastes as Substrate,” Biotechnol Lett, 31, (May 23, 2009), (7 pages).

Waks, Z., et al., “Engineering a Synthetic Dual-Organism System for Hydrogen Production,” Applied and Environmental Microbiology, vol. 75, No. 7, (Apr. 2009), (9 pages).

Wang, A., et al., “Biohydrogen Production from Anaerobic Fermentation,” Adv Biochem Engin/Biotechnol, 128, (2012), (21 pages).

Wang, J., et al., “Clostridium Species for Fermentative Hydrogen Production: An Overview,” International Journal of Hydrogen Energy, 46, (2021), (27 pages).

Yasin, N., et al., “Microbial Characterization of Hydrogen-Producing Bacteria in Fermented Food Waste at Different pH Values,” International Journal of Hydrogen Energy, 36, (Aug. 2011), (12 pages). x.

* cited by examiner

*Primary Examiner* — Satyendra K Singh

(74) *Attorney, Agent, or Firm* — Hartman Global IP Law; Gary M. Hartman; Domenica N.S. Hartman

(57) ABSTRACT

Processes and systems for biologically producing hydrogen gas from organic waste, including food waste. Such a process includes biologically producing hydrogen gas from organic waste by anaerobic fermentation of the organic waste with at least one strain of yeast.

17 Claims, 10 Drawing Sheets

PROCESSES AND SYSTEMS FOR BIOLOGICAL HYDROGEN PRODUCTION FROM ORGANIC WASTE USING YEAST

CROSS-REFERENCE TO RELATED APPLICATIONS

This is a continuation-in-part patent application of co-pending U.S. patent application Ser. No. 17/763,761 filed Mar. 25, 2022, which claims priority to International Patent Application No. PCT/US2020/052812 filed Sep. 25, 2020, which claims the benefit of U.S. Provisional Application No. 62/906,261 filed Sep. 26, 2019. The contents of these prior patent documents are incorporated herein by reference.

STATEMENT REGARDING FEDERALLY SPONSORED RESEARCH OR DEVELOPMENT

This invention was made with government support under Contract No. DE-FG36-06GO86050 awarded by the U.S. Department of Energy. The government has certain rights in the invention.

BACKGROUND OF THE INVENTION

The present invention generally relates to the biological production of hydrogen, and particularly relates to the biological production of hydrogen gas from organic waste using yeast.

Biological production of hydrogen gas offers a sustainable process for the production of fuel with a concurrent minimization of waste. Hydrogen gas has significant advantages as a clean energy source. Unlike fossil fuels, combustion of hydrogen does not produce carbon dioxide or oxides of nitrogen and sulfur. Hydrogen also has a higher energy yield (as an example, about 120 kJ/g) than hydrocarbons (as an example, about 44 kJ/g for petroleum). By using hydrogen in a fuel cell or a reciprocating engine, the major end products are electricity, water, and heat.

There are, however, technical and economic concerns with the production and storage of hydrogen impacting its near term viability. Conventional chemical processes for hydrogen production are energy intensive and therefore not cost effective. Biological hydrogen production processes offer a potentially economic and sustainable alternative for producing hydrogen. The use of microbial organisms is currently attracting increasing interest as a means of producing hydrogen, as indicated in multiple recent publications. Numerous studies have been conducted using microorganisms to generate hydrogen from fermentation of various substrates, nonlimiting examples of which are reported in Kapdan et al., "Bio-hydrogen Production from Waste Materials," Enzyme Microbial Technology, 38(5): 569-582 (2006), and Chen et al., "Using Sucrose as a Substrate in an Anaerobic Hydrogen-producing Reactor," Adv. Environ Res 7:695-699 (2003). Some studies have used a pure culture of bacteria, such as species of *Bacillus, Clostridium*, and *Enterobacter*, while others have used mixed cultures that originated from sludge, animal wastes, sewage, compost, soil, etc. Kummaravel et al., "Influence and Strategies for Enhanced Biohydrogen Production from Food Waste," Renewable and Sustainable Energy Reviews 92: 807-822 (2018), provides a survey of processes to produce hydrogen from food waste. Using organic wastes for bio-production of hydrogen not only has the potential to generate cost effective and renewable energy but also can reduce pollution in the environment.

BRIEF DESCRIPTION OF THE INVENTION

The intent of this section of the specification is to briefly indicate the nature and substance of the invention, as opposed to an exhaustive statement of all subject matter and aspects of the invention. Therefore, while this section identifies subject matter recited in the claims, additional subject matter and aspects relating to the invention are set forth in other sections of the specification, particularly the detailed description, as well as any drawings.

The present invention provides, but is not limited to, processes and systems for biologically producing hydrogen gas from organic waste, including food waste.

According to a nonlimiting aspect of the invention, a process includes biologically producing hydrogen gas from organic waste by anaerobic fermentation of the organic waste with at least one strain of yeast.

According to another nonlimiting aspect of the invention, a system for performing a process as described above. The system includes a reaction tank in which the anaerobic fermentation is performed, a source of at least one strain of yeast, and means for introducing the at least one strain of yeast to the reaction tank. The reactor tank is at a pressure of not greater than 12 Pa above atmospheric pressure, an oxygen level of less than 0.25%, and a controlled elevated temperature.

Technical aspects of processes and systems as described above preferably include the ability to use yeast, as opposed to only bacteria, in a process that significantly increases hydrogen production as well as reduces processing and operating requirements, including minimal preprocessing of the organic waste and simplified operating conditions during hydrogen production.

Other aspects and advantages of this invention will be appreciated from the following detailed description as well as any drawings.

DETAILED DESCRIPTION OF THE INVENTION

Figure 1:
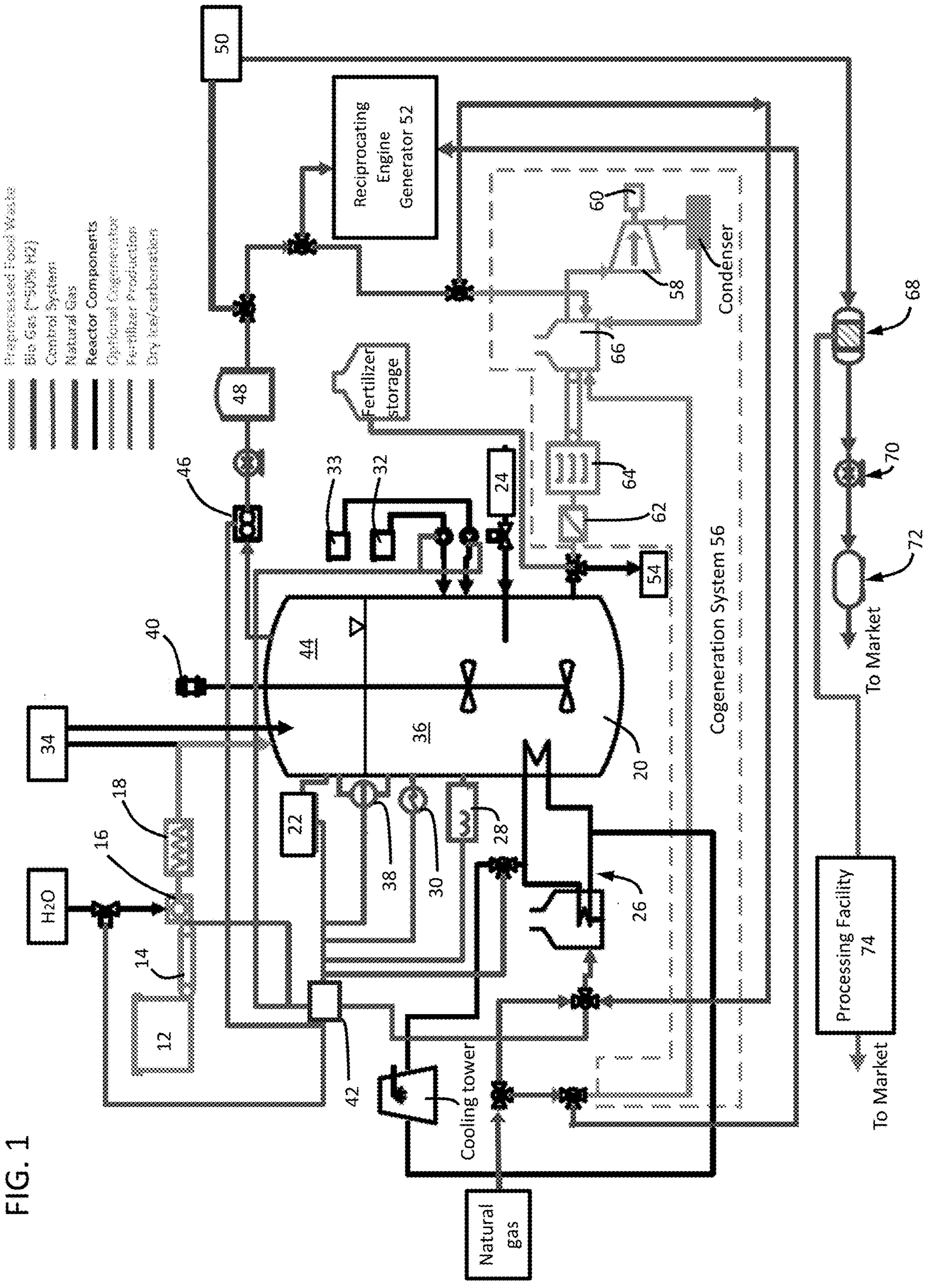
FIG. 1 schematically represents a system for biologically producing hydrogen gas from organic waste by anaerobic fermentation with at least one strain of yeast in accordance with a nonlimiting embodiment of this invention.

The following disclosure describes various aspects of processes and systems for biologically producing hydrogen gas from organic waste by anaerobic fermentation. A nonlimiting example of such a system is schematically represented in FIG. 1. The system represents an approach to producing hydrogen biologically from organic waste that employs yeast to increase hydrogen production as compared to processes utilizing only bacteria. Yeast particularly suitable for use in systems and processes as described herein include those suitable for use in the commercial production of wine and ethanol, as examples, *Saccharomyces cerevisiae* and species of the genus *Schizosaccharomyces*, although other strains of yeast also have shown hydrogen production capability. During investigations leading to the present invention, it was determined that the use of certain yeasts in the system schematically represented in FIG. 1 has the ability to significantly increase productivity as well as reduce processing and operating requirements if the anaerobic fermentation process is performed within certain relatively narrow ranges of processing parameters. Minimal preprocessing is required for the organic waste and, aside from adhering to certain relatively narrow ranges of processing parameters, the operating conditions during hydrogen production are greatly simplified.

Generally, the nonlimiting embodiment of FIG. 1 represents organic waste (feedstock) as being delivered by a conveyor 14 from a receiving tank 12 to a grinder 16 where the waste is comminuted, and then fed to a reactor tank 20 with a screw pump 18. The reactor tank 20 is sealed and maintained at a low pressure, above atmospheric pressure but preferably not greater than about 0.25 psi (about 12 Pa) above atmospheric pressure. FIG. 1 further indicates that water ($H_2O$), for example, tap water, is combined with the waste within the grinder 16. The pressure within the tank 20 is monitored with a pressure transducer 22. At startup, a sparge gas 24 is introduced into the tank 20 to produce anaerobic conditions within the tank 20. The sparge gas 24 selected to be inert to the anaerobic fermentation process, as a nonlimiting example, nitrogen. Also at startup, an acid 33, as a nonlimiting example, sulfuric acid ($H_2SO_4$), is preferably added to the reactor 20 to achieve a desired initial pH. The temperature of the waste within the tank 20 is controlled, for example, by a heater 26 and thermostat 28, and the pH within the tank 20 is monitored with a pH meter 30 and controlled through the introduction of a base 32, as a nonlimiting example, a technical grade of sodium hydroxide (NaOH). FIG. 1 represents yeast 34 as being introduced into the tank 20 directly and/or with the comminuted waste (waste and water) to form what is referred to herein as a mixture 36. The level of the mixture 36 within the tank 20 can be monitored with a level sensor 38. While within the tank 20, the mixture 36 is preferably agitated, for example, with a stirring apparatus 40.

The system represented in FIG. 1 may be operated in either a batch or continuous mode. Outputs of the pressure transducer 22, thermostat 28, pH meter 30, and level sensor 38 and control of the heater 26 and introduction of the waste, water, sparge gas 24, base 32, and yeast 34 into the tank 20 can all be supplied to a suitable processor 42.

FIG. 1 represents gaseous products (bio gas) 44 of anaerobic fermentation within the tank 20 as drawn from an upper end of the tank 20 through a flow meter 46, which is also monitored with the processor 42. The gaseous products 44 contain hydrogen gas, and the composition of the gaseous products 44 is preferably analyzed and confirmed, for example, using a gas chromatograph (not shown). The gaseous products 44 may undergo compression before being collected in a tank 48, from where the gaseous products 44 may be sold or utilized by downstream process applications 50, routed to a generator 52, and/or routed to the heater 26 as a fuel source. FIG. 1 represents an example of the process applications 50 as including a gas separator 68 that separates hydrogen gas from the gaseous products 44, which may then be compressed with a compressor 70 and placed in a tanker 72 for transport.

Residual waste 54 is drawn from the tank 20. The residual waste 54 may be placed in a landfill or used as a fertilizer. Alternatively or in addition, FIG. 1 represents the residual waste 54 used as a fuel source for a distributed cogeneration system 56 that produces electrical power with a turbine 58 and generator 60. For this purpose, the residual waste 54 is shown as drawn through a strainer 62 and dryer 64 before being delivered to a boiler 66 fueled by natural gas. Byproducts of the turbine 58 may be condensed before being returned to the boiler 66.

In addition to hydrogen gas, carbon dioxide is a coproduct of the process performed by the system of FIG. 1. Hydrogen gas may constitute about 50% or more of the gaseous products 44 of the process with the remainder (e.g., about 50% or less) being carbon dioxide. An $H_2/CO_2$ mixture containing about 50% or more of hydrogen gas can be used to produce heat by direct combustion, or directly produce electricity in a reciprocating engine-driven generator, or produce electricity in a fuel cell after additional processing. In FIG. 1, the process applications 50 are represented as further including a carbon dioxide processing facility 74, such as a dry ice and/or carbonation plant, where the carbon dioxide separated from the gaseous products 44 by the gas separator 68 may be productively utilized.

While carbon dioxide is of concern as a greenhouse gas, carbon dioxide is much less of an environmental issue than methane ($CH_4$), which is internationally the most common product for organic waste digesters. If the source of the feedstock is food waste, the food crops that were the original source of the food waste may consume an equal or greater amount of carbon dioxide during normal growth than is released by the anaerobic fermentation of the food waste, in which case the process performed with the system of FIG. 1 is at least neutral from a carbon balance perspective.

Figure 2:
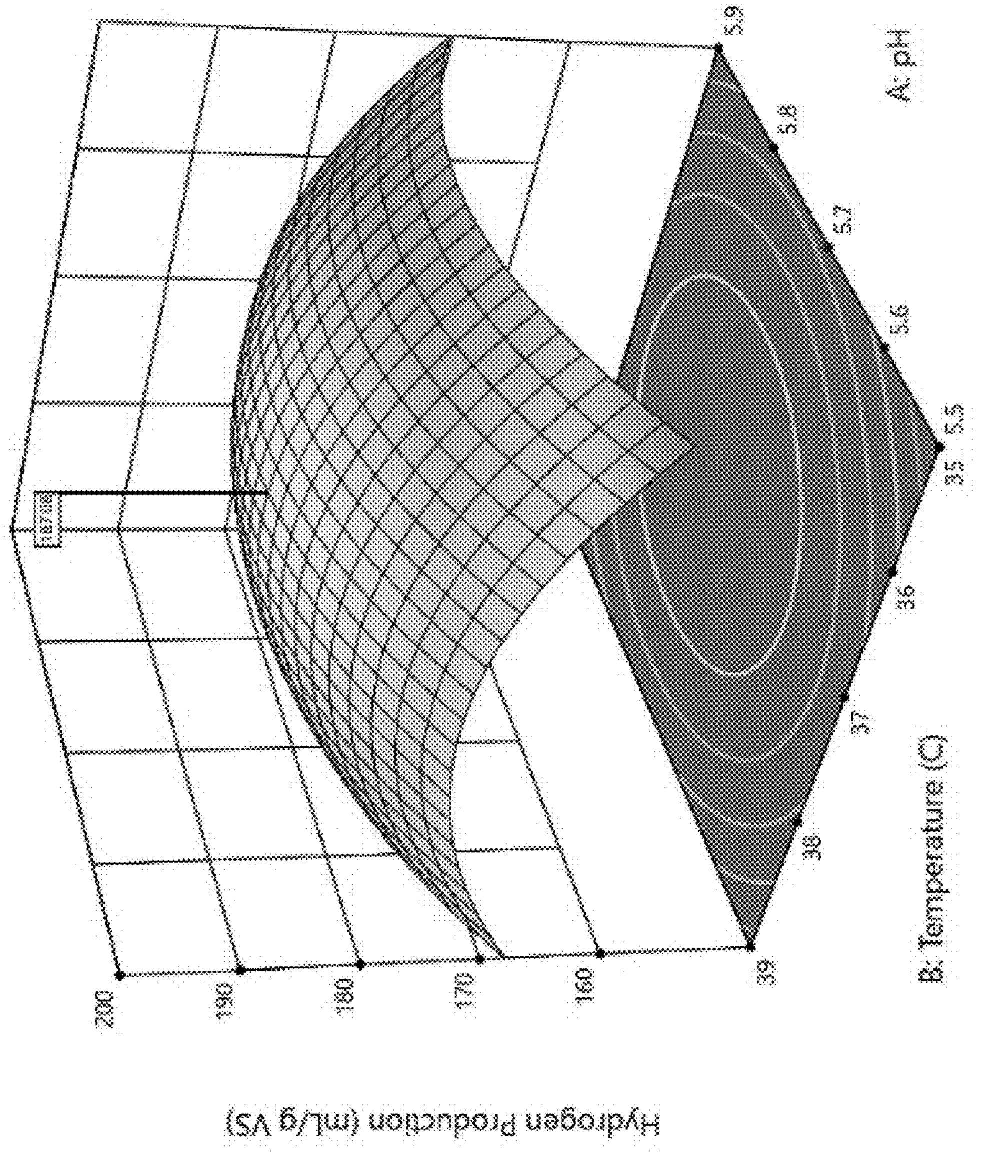
FIG. 2 is a graph plotting a response surface with temperature and pH as factors for a standardized food waste.
Figure 3:
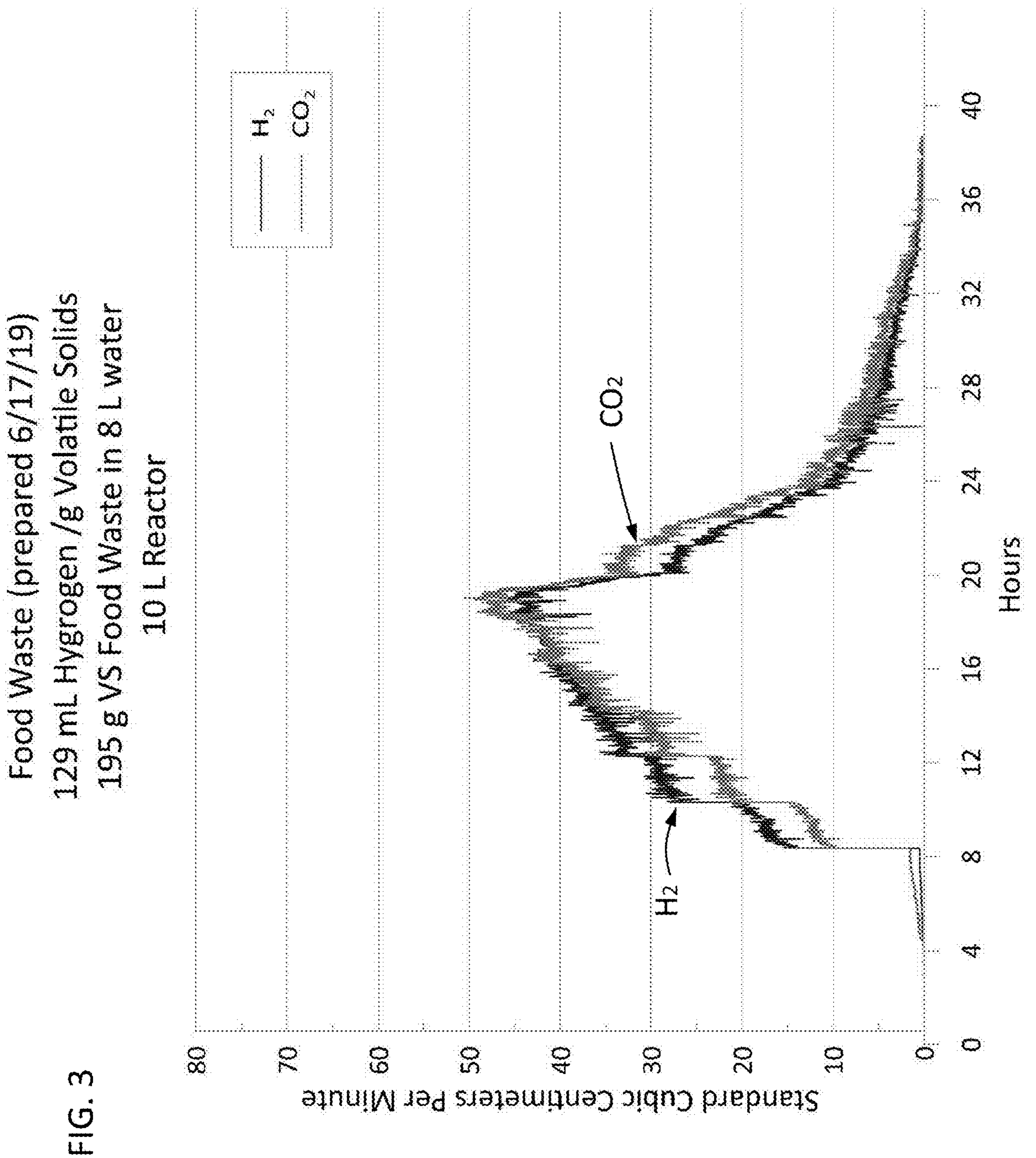
FIGS. 3 and 4 are graphs plotting gas production data obtained with systems of the type represented in FIG. 1.

Because yeasts used by the anaerobic fermentation process, as examples, *Saccharomyces cerevisiae* and species of the genus *Schizosaccharomyces*, are well known for use in winemaking, baking, brewing and ethanol production, notable aspects of the process performed with the system involve operating the system at specific conditions that will maximize production of hydrogen as opposed to methane or ethanol. Hydrogen production was significantly increased by employing operating conditions that were determined through the use of statistical analysis and specifically a central composite design and an associated response surface. Temperature and pH were identified as the operating parameters that had the most influence on hydrogen production levels for the tested food waste. The response surface considering temperature and pH as factors for a standardized food waste is shown in FIG. 2 for the case of a 10-liter reaction tank. These results were used to determine operating conditions capable of maximizing hydrogen production. Additional sensitivity studies were used to estimate the influence of variations in food composition and to implement methods for blending food sources to maintain high levels of hydrogen production. In a first investigation, about 200 g (dry equivalent) of food waste was combined with 8 liters of tap water in a 10-liter reaction tank. The tank had a head space above the waste-water mixture of about 2.75 liters. The food waste did not undergo any preprocessing other than grinding in a standard blender. In the tank, the waste-water mixture was combined with a commercial yeast used in ethanol production and agitated by stirring at about 130 RPM with a 4-cm diameter stirring paddle. The tank was maintained at a temperature of 37° C., at a pressure slightly above atmospheric pressure, and at a pH of 5.7 by means of a pump fed solution of technical grade sodium hydroxide. Gas flow from the tank was measured with a mass flow meter. Gas composition was measured with a micro gas chromatograph (CP-4900 Dual Channel Micro-GC; Varian Inc.). Pressure within the tank was continuously measured with a pressure transducer (Omega PX139) and recorded. The composition of the gaseous products drawn from the head space was determined and recorded every two hours with the gas chromatograph and mass flow meter and is plotted in FIG. 3.

The investigation evidenced that hydrogen can be biologically produced from organic waste using a process that employs yeast rather than bacteria alone as the basis for anaerobic fermentation. The majority of the hydrogen was produced within a 36-hour period. In contrast, processes for producing methane from organic waste can require weeks of fermentation time, and processes that produce hydrogen from organic waste using bacteria often require roughly double this time. As such, the investigation indicated that the process is capable of short production times to greatly increase productivity and value and allow for an associated reduction in production facility size. Complexity of a production facility implementing the system represented in FIG. 1 is also reduced because of the use of yeast and the determined process operating parameters.

In a second investigation, a food waste was synthesized with food materials described in Table 1.

TABLE 1

| Food Material | Mass (g) | Total Carbo-hydrate (mass %) | Total Fat (mass %) | Protein (mass %) | Fiber (mass %) |
|---|---|---|---|---|---|
| Dry Oatmeal | 575 | 67.5 | 7.5 | 12.5 | 10 |
| Bread | 614 | 45.6 | 2.6 | 8.8 | 3.5 |
| Mixed Vegetable | 472 | 13.3 | 0 | 2.2 | 3.3 |
| Carrot Juice | 935 | 6.8 | 0 | 0.9 | 0.4 |
| Raw Cabbage | 414 | 5.8 | 0 | 1.3 | 2.5 |

Figure 4:
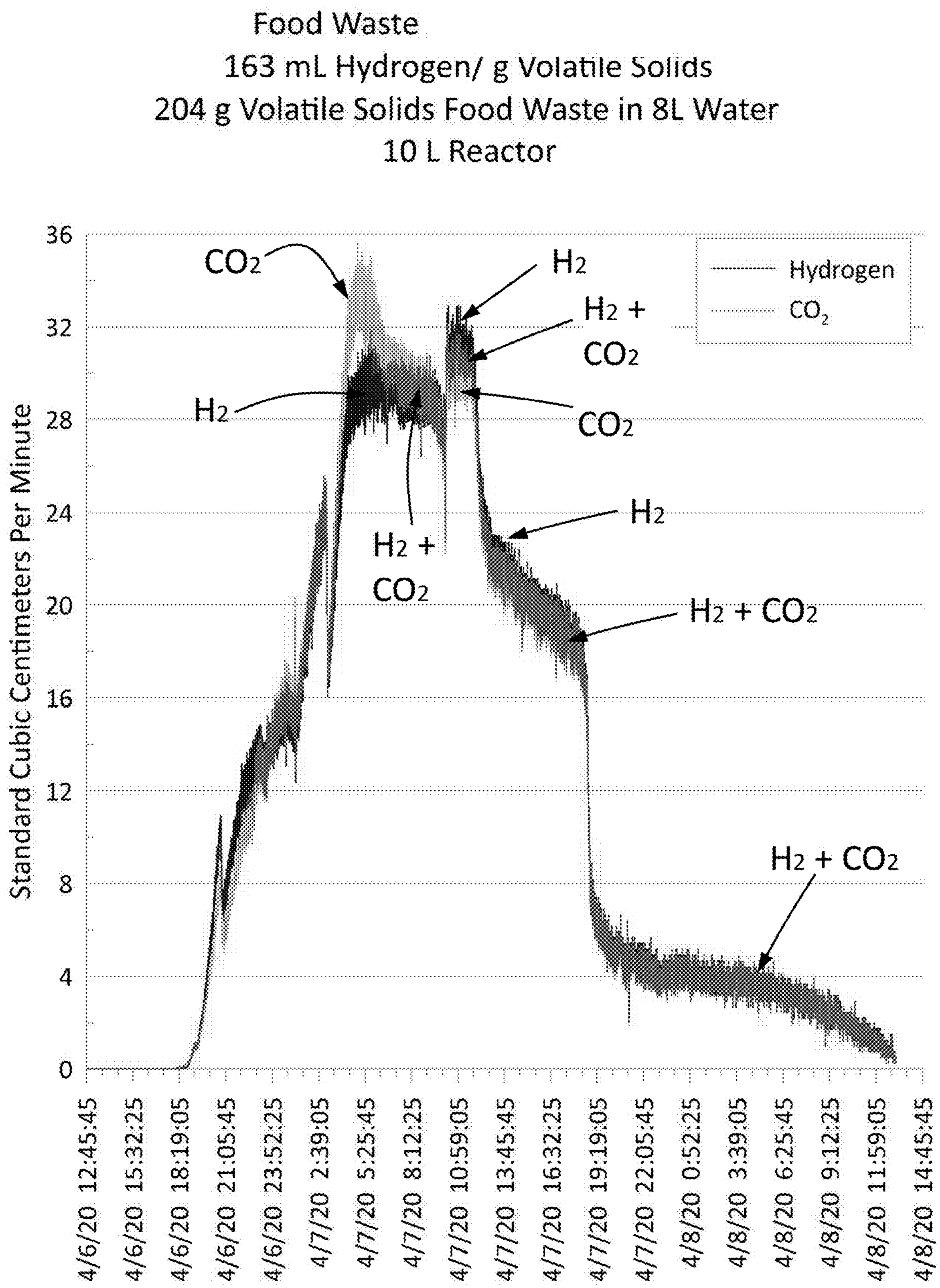

As with the first investigation, the food waste did not undergo any preprocessing other than grinding after being combined with water. In a 10-liter reactor tank, the waste-water mixture was combined with a commercial yeast used in ethanol production and agitated by stirring at about 120 RPM. The tank was maintained at a temperature of 37° C., at a near-atmospheric pressure of not greater than 0.25 psi (about 12 Pa) above atmosphere, and at a pH of 5.7 by means of a pump fed solution of technical grade sodium hydroxide. The production output of this process is plotted in FIG. 4, which shows a significant increase in hydrogen production compared to initial values. The data of FIG. 4 also evidence that hydrogen production rate using the system of FIG. 1 has been increased by a factor of approximately twelve over initial 100 mL reactor bacteria-based approaches (principally *Clostridium*). In addition, the time required for hydrogen production was decreased for the bulk of the gas production, and the concentration of hydrogen in the produced biogas had increased from 25% for initial bacteria-based approaches to approximately 50% in the investigations reported above.

In a third investigation, a food waste was synthesized with food materials described in Table 2. This mass of food material was added to 1 liter of water and the mixture was then ground. Approximately 1250 grams of the ground food waste was then added to the reactor containing 7 liters of water for processing.

TABLE 2

| Food Material | Mass (g) | Total Carbohydrate (mass %) | Total Fat (mass %) | Protein (mass %) | Fiber (mass %) |
|---|---|---|---|---|---|
| Dry Oatmeal | 227 | 67.5 | 7.5 | 12.5 | 10 |
| Corn | 227 | 23.3 | 1.1 | 2.2 | 2.2 |
| Mixed Vegetable | 227 | 13.3 | 0 | 2.2 | 3.3 |

Figure 5:
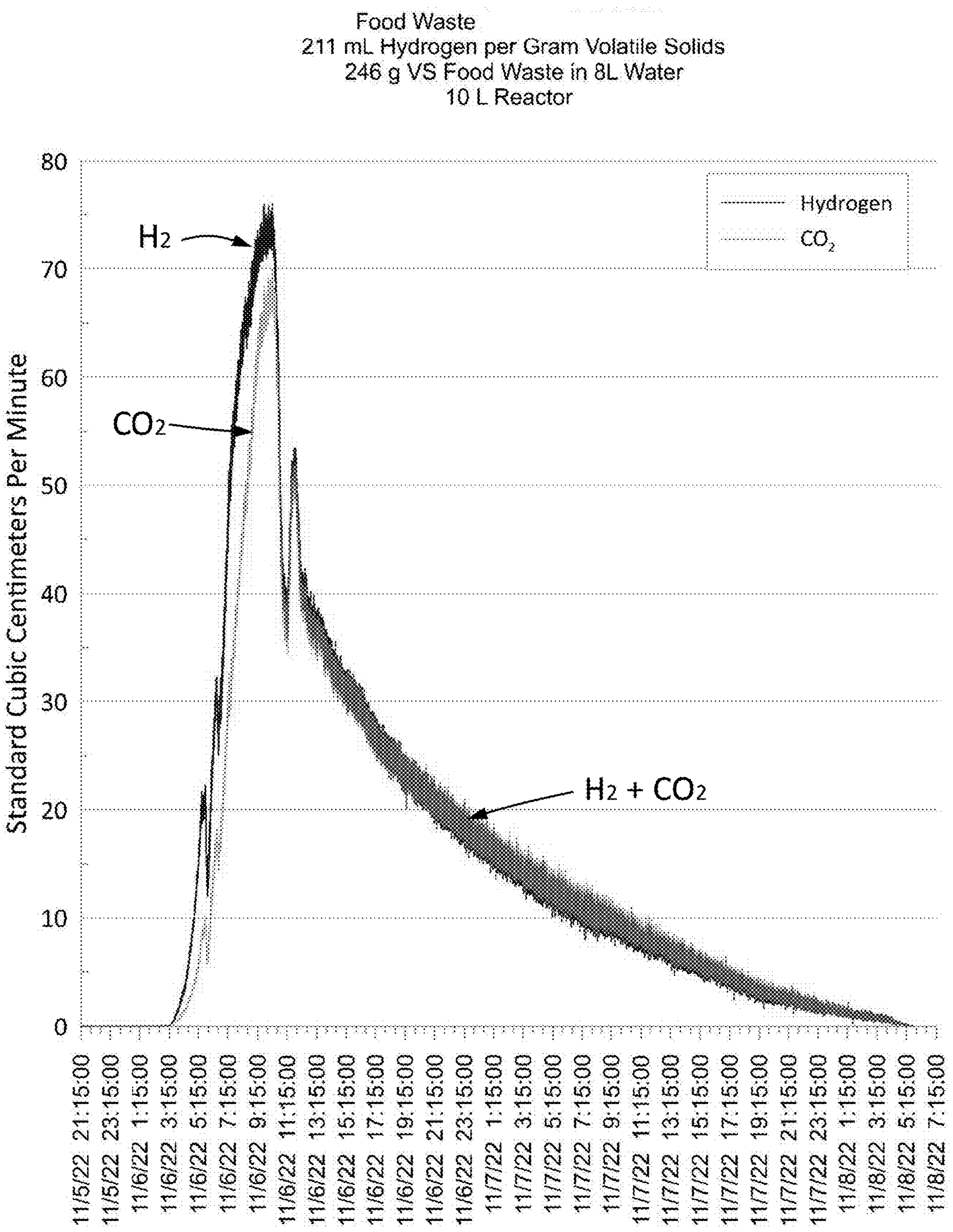
FIG. 5 is a graph of hydrogen production optimized with yeast addition using a system of the type represented in FIG. 1.
Figure 7:
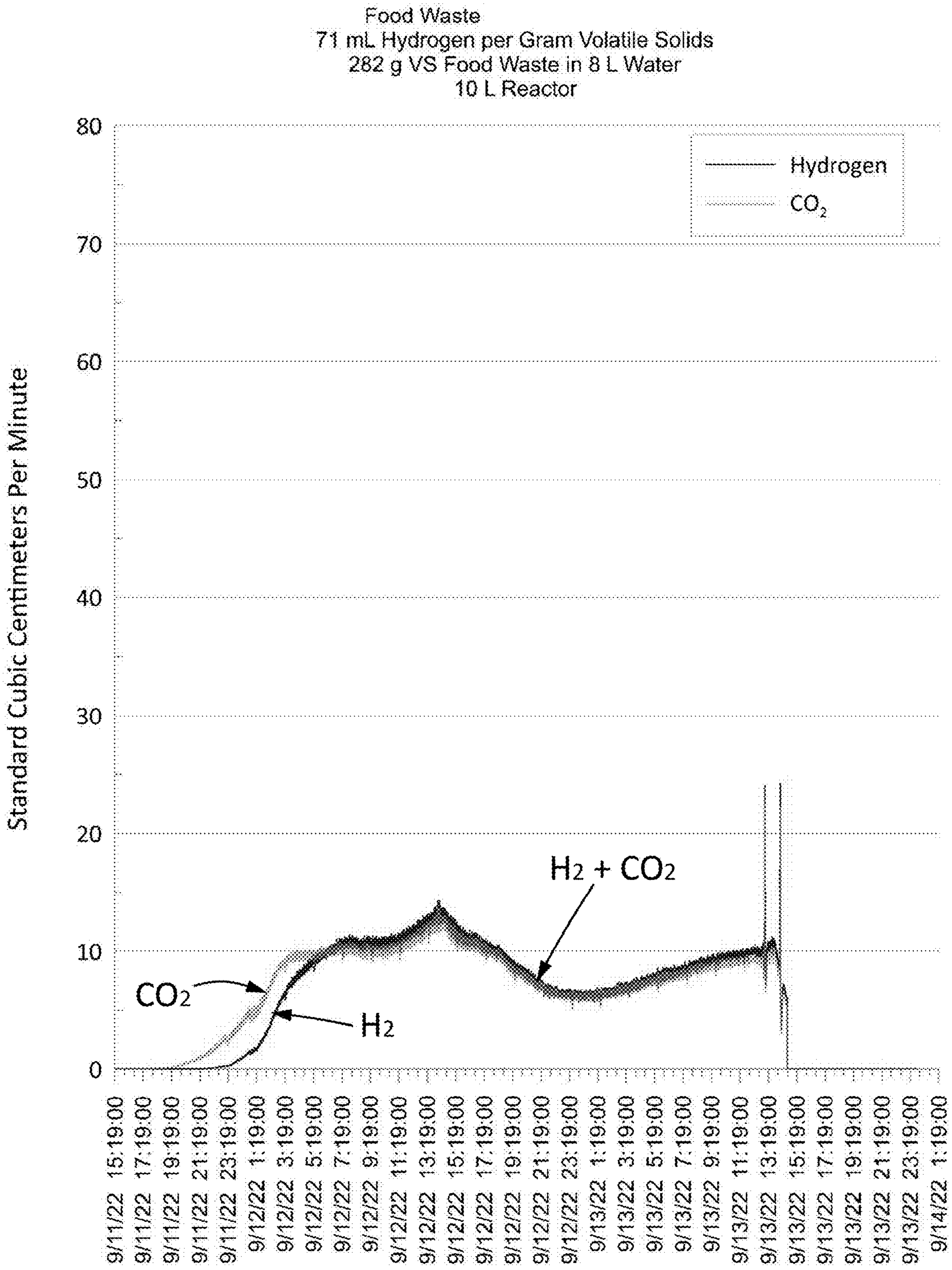
FIG. 7 is a graph of hydrogen production without pH control using a system of the type represented in FIG. 1.
Figure 8:
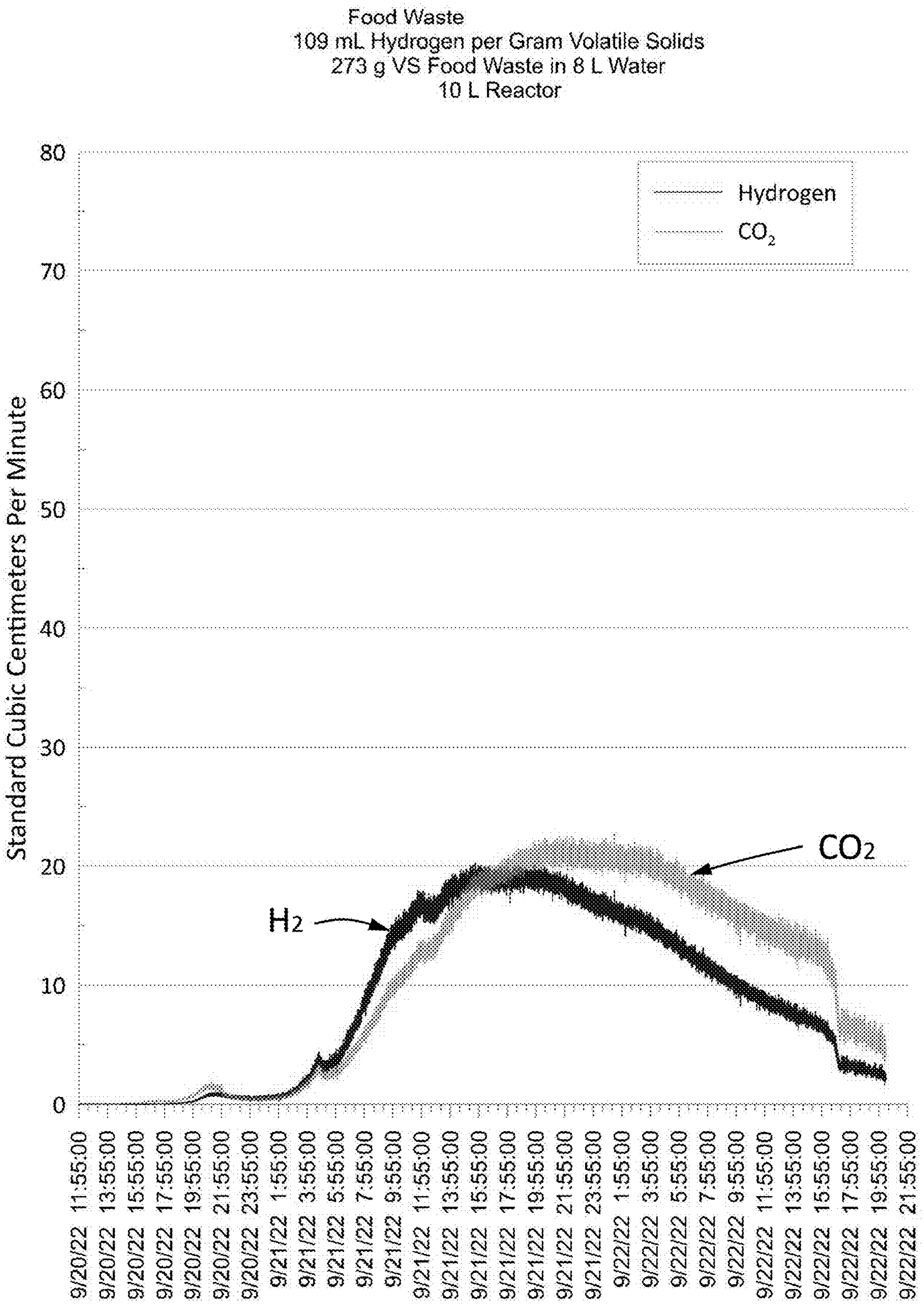
FIG. 8 is a graph of hydrogen production without the addition of yeast using a system of the type represented in FIG. 1.

As with the second investigation, the food waste did not undergo any preprocessing other than grinding after being combined with water. In a 10-liter reactor tank, the waste-water mixture was combined with a commercial yeast used in wine production and agitated by stirring at about 120 RPM. The tank was maintained at a temperature of 37° C., at a near-atmospheric pressure of not greater than 0.25 psi (about 12 Pa) above atmosphere, and at a pH of 5.7 by means of a pump fed solution of technical grade sodium hydroxide. The initial pH of the food waste was adjusted to approximately 6.0 with the addition of sulfuric acid. This adjustment results in a decrease in the latency period as can be observed by comparing FIG. 5 with FIG. 3. Approximately 0.1 gram of ferrous sulfate was added to the reactor initially to increase the presence of iron ions and thereby increase productivity. The composition of the food waste is dependent on the date and location of harvest. As a result, the naturally occurring bacteria consortia in the food waste can vary from sample to sample. To reduce this variation and to assure consistency between food samples, 0.5 mL of *Clostridium acetobutylicum* culture was added to the reactor initially after sparging the vessel with nitrogen. Approximately 0.5 g of yeast is again added to the reactor slightly before the peak of the production curve. This resulted in a broadening of the production peak and thereby increased production at an earlier time in the process. The peak in the curve is predicted using a polynomial curve fit done approximately 8 hours after the start of the process. The production output for this case is plotted in FIG. 5, which shows a significant increase in hydrogen production compared to previous values. In addition, the latency period was decreased and the time required for hydrogen production was maintained at less than 36 hours for the bulk of the gas production. The optimization of hydrogen production for this process can be observed by comparing FIG. 5 with FIG. 8, which is a case without addition of yeast, and FIG. 7 which is a case without pH control. The shape of the hydrogen production curve is an important aspect when considering options for commercial scale up. Production curves with higher initial production levels and reduced latency time result in a decrease in the required reactor size for a specific hydrogen production rate as well as reduced feed material feed requirements. The latency period for FIG. 8 is approximately fourteen hours while the latency period for FIG. 5 using this process is approximately six hours.

In a fourth investigation the reactor vessel size was increased to 159 liters. Food waste was synthesized with food materials described in Table 3

TABLE 3

| Food Material | Mass (kg) | Total Carbohydrate (mass %) | Total Fat (mass %) | Protein (mass %) | Fiber (mass %) |
|---|---|---|---|---|---|
| Dry Oatmeal | 2.7 | 67.5 | 7.5 | 12.5 | 10 |
| Corn | 2.7 | 45.6 | 2.6 | 8.8 | 3.5 |
| Mixed Vegetable | 2.7 | 13.3 | 0 | 2.2 | 3.3 |

Figure 6:
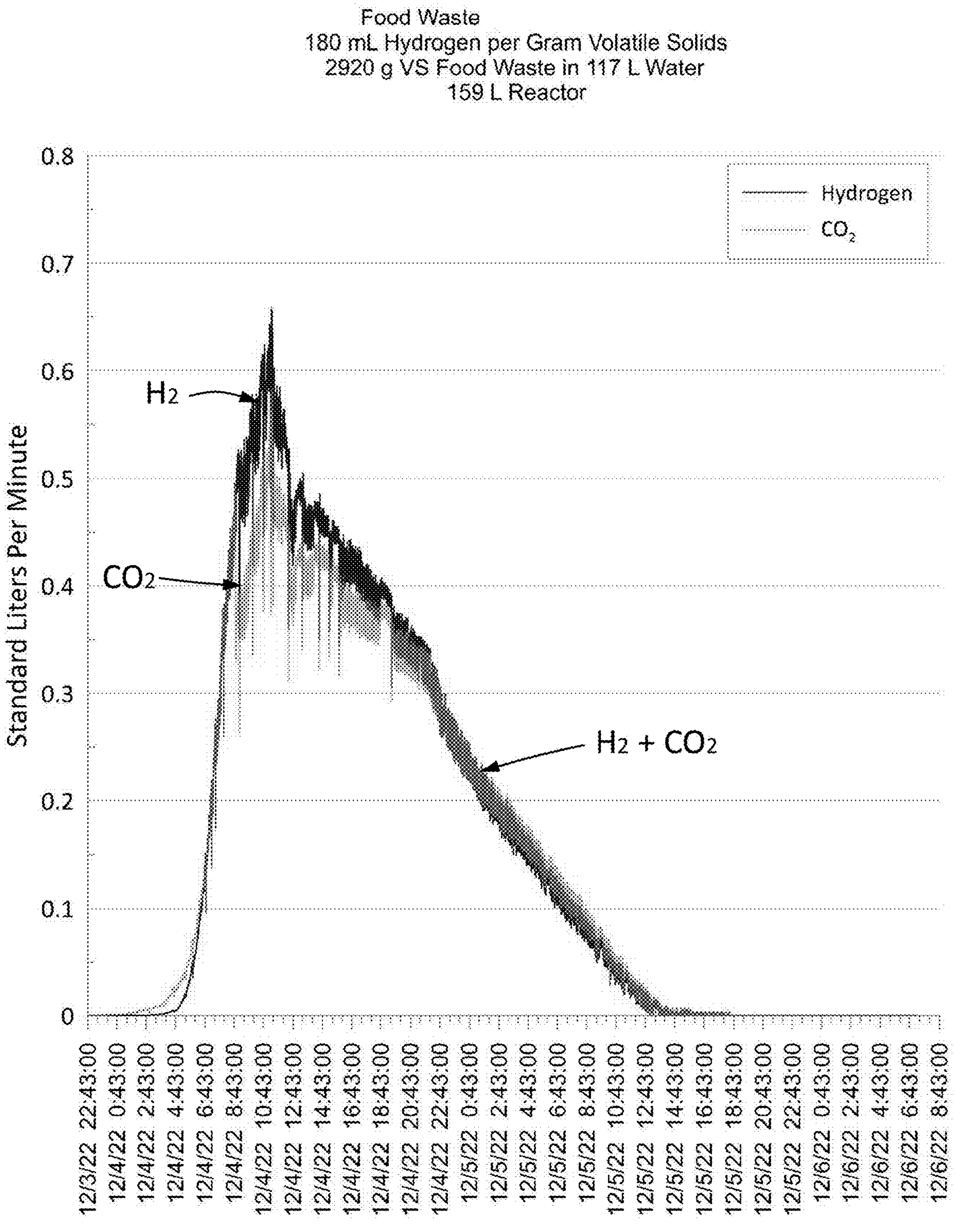
FIG. 6 is a graph of hydrogen production optimized with yeast addition for a scaled-up reactor using a system of the type represented in FIG. 1.
Figure 9:
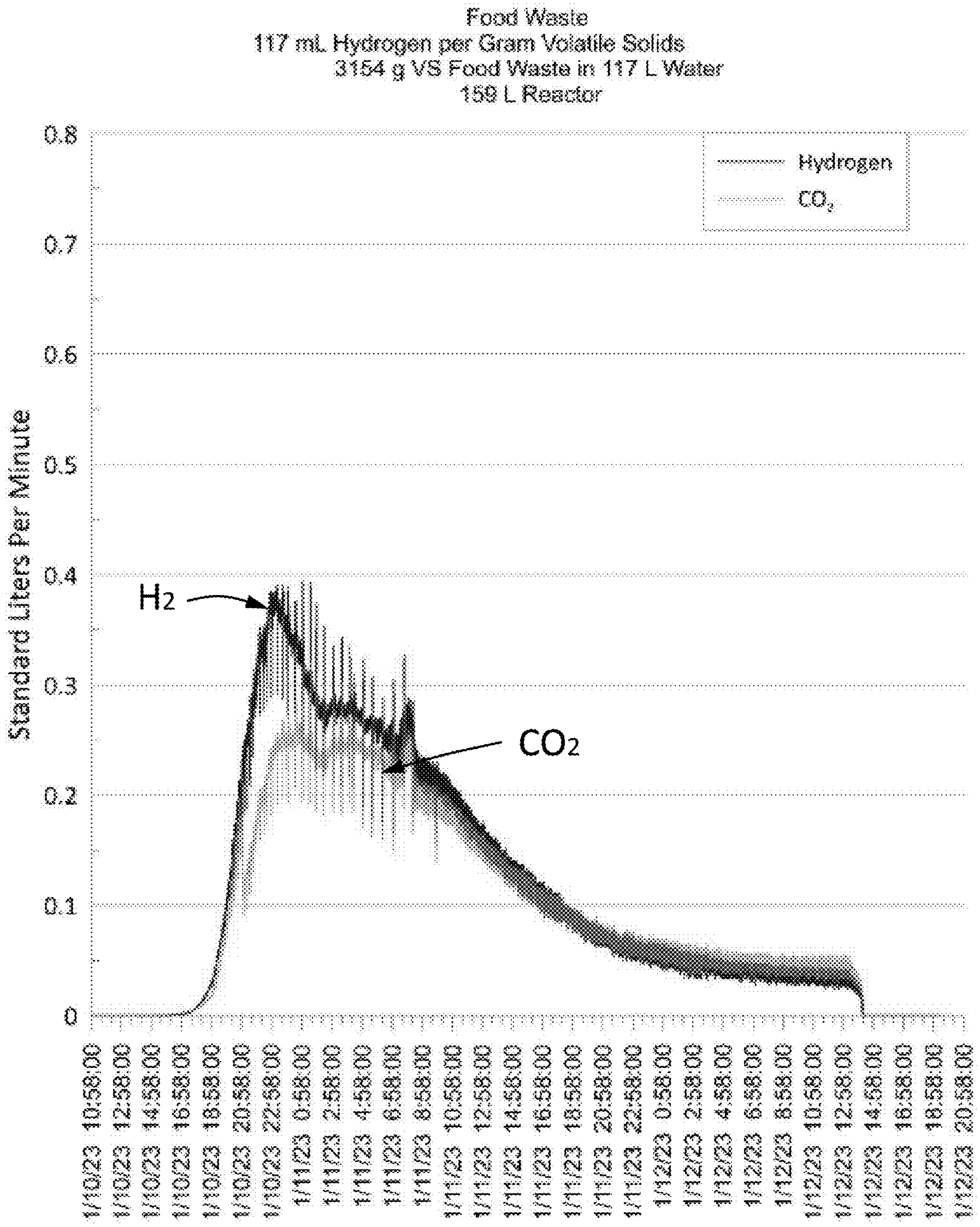
FIG. 9 is a graph plotting hydrogen production with a food waste containing essentially no sugar.
Figure 10:
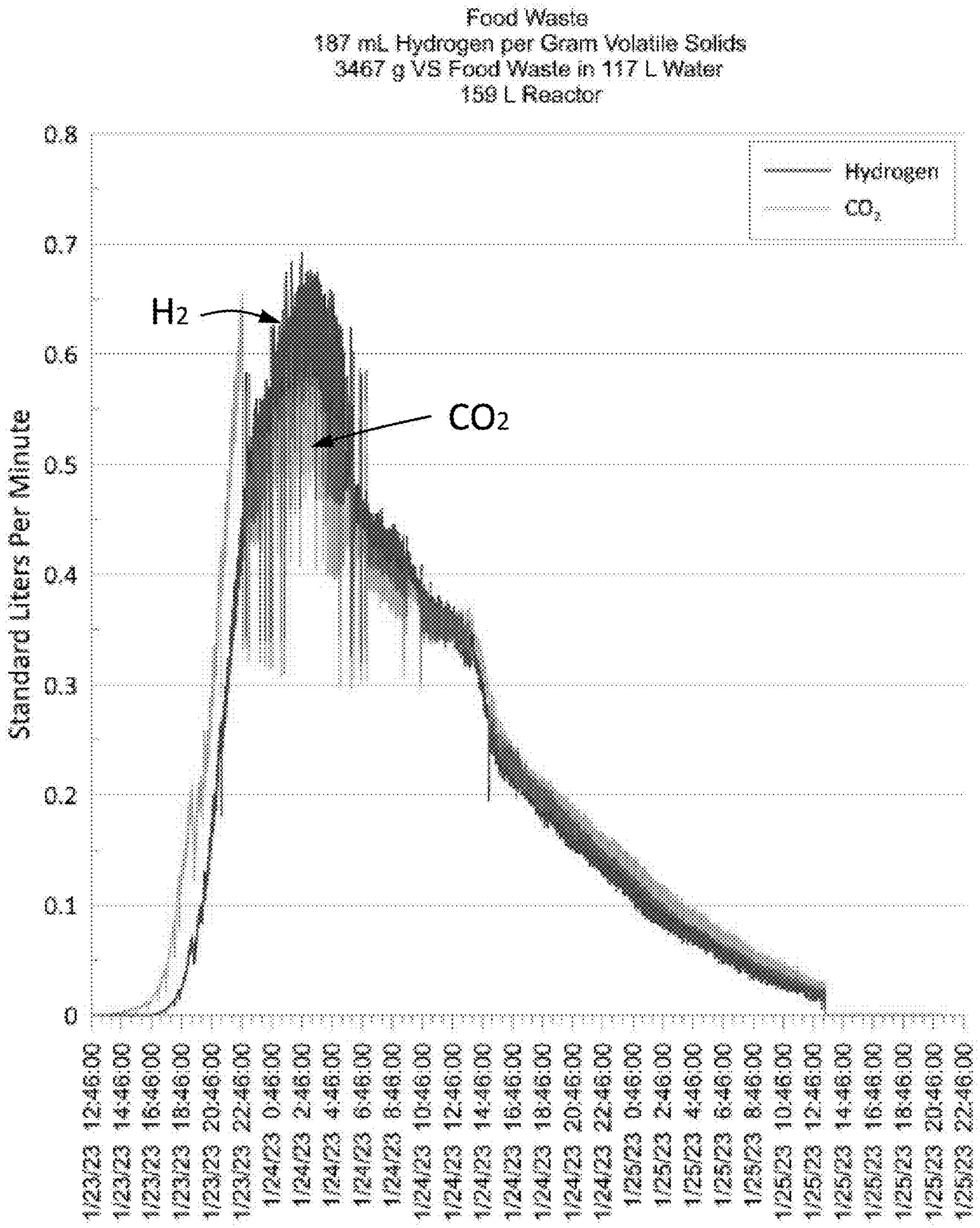
FIG. 10 is a graph plotting hydrogen production with the same food waste as FIG. 9 to which dextrose was added at the start of the reaction.

This mass of food material was added to 19 liters of water and the mixture was then ground. Approximately 19 kg of the ground food waste and water mixture was then added to the reactor containing 114 liters of water for processing. As with the second investigation, the food waste did not undergo any preprocessing other than grinding after being combined with water. About 3.5 kg (dry equivalent) of food waste was combined with 133 liters of tap water in the reaction tank. The tank had a head space above the waste-water mixture of about 27 liters. The food waste did not undergo any preprocessing other than grinding in a standard blender. In the tank, the waste-water mixture was combined with either a commercial yeast used in winemaking or a yeast used in ethanol production and agitated by a counter flow fluid circulating system driven by an adjustable speed flexible impeller pump. The tank was maintained at a temperature of 37° C., at a pressure slightly above atmospheric pressure, and at a pH of 5.7 by means of a pump fed solution of technical grade sodium hydroxide. The initial pH of the food waste was adjusted to approximately 6.0 by the addition of 2 M sulfuric acid. This adjustment results in a decrease in the latency period as shown in FIG. 6 when compared to FIG. 3. Approximately 1.0 gram of ferrous sulfate was added to the reactor initially to increase the presence of iron ions and thereby increase productivity. The composition of the food waste is dependent on the date and location of crop harvest. As a result, the naturally occurring bacteria consortia and sugar content in the food waste can vary from sample to sample. To ensure consistency between food samples, 5 mL of *Clostridium acetobutylicum* culture was added to the reactor initially. Slightly before the peak of the production curve, approximately 5 grams of yeast is again added to the reactor. This resulted in a broadening of the production peak and thereby increases production at an earlier time in the process. The peak in the curve is predicted using a polynomial curve fit done approximately eight hours after the start. Gas flow from the tank was measured with a mass flow meter. Gas composition was measured with a micro gas chromatograph (CP 4900 Dual Channel Micro GC; Varian Inc.). Pressure within the tank was continuously measured with a pressure transducer (Omega PX139) and recorded. The composition of the gaseous products drawn from the head space was determined and recorded every two hours with the Gas Chromatograph. Mass flow rates for hydrogen and carbon dioxide are calculated from the total mass flow rate and the gas composition obtained from the gas chromatograph and mass flow meter. The production output of this process is plotted in FIG. 6, which shows a significant increase in hydrogen production compared to initial values. In addition, the time required for hydrogen production was maintained at less than 36 hours for the bulk of the gas production. For cases of food waste that resulted from crops that were harvested in late summer or fall, when there is less sugar content, it was possible to increase hydrogen production by adding dextrose to the reactor. For lower sugar content food waste cases for the 159 liter reactor the addition of 200 g of dextrose at the start provided the maximum increase in hydrogen production as can be observed by comparing FIG. 9, which is a case with all rice (essentially no sugar), and FIG. 10 which is a case with 200 g dextrose added to standard food waste. Lesser or greater amounts of dextrose resulted in decreased production. Similar addition of fructose or sucrose resulted in lesser additional hydrogen production. Assuming the process scales linearly, for the sample shown in FIG. 6 a 25,000-gallon (about 94,635-liter) reactor tank could produce approximately 328,000 liters of hydrogen at atmospheric pressure (STP) in approximately twenty-four hours.

Additional investigations have evidenced that the results reported above can be obtained if the process is carried out with certain relatively narrow ranges of processing parameters. The temperature range should be maintained in a range of about 32° C. to about 42° C. and the pH should be maintained in a range of about 5.5 to 5.9 pH to achieve appreciable hydrogen production. Agitation is also believed to be important, as is maintaining a positive pressure that is slightly above atmospheric pressure, preferably not greater than 0.25 psi (12 Pa) above atmospheric pressure. Identified yeasts used in ethanol or wine production performed better than yeasts conventionally used in brewing and standard bread yeasts. Because the process is anaerobic, an inert purge gas is employed as indicated in FIG. 1, and oxygen levels within the reactor tank are preferably initially less than 0.25%. Finally, in evident from the above-described investigations, the anaerobic fermentation can be performed without intentional additions of bacteria to the organic waste, or can be performed with intentional additions of bacteria to the organic waste.

While the invention has been described in terms of particular embodiments and investigations, it should be apparent that alternatives could be adopted by one skilled in the art. For example, the process system and its components could differ in appearance and construction from the embodiments described herein and shown in the drawings, and functions of certain components of the process system could be performed by components of different construction but capable of a similar (though not necessarily equivalent) function, certain process parameters could be modified, and appropriate materials could be substituted for those noted. As such, it should be understood that the intent of the above detailed description is to describe the particular embodiments represented in the drawings and certain but not necessarily all features and aspects thereof, and to identify certain but not necessarily all alternatives to the particular embodiments represented in the drawings. As a nonlimiting example, the invention encompasses additional or alternative embodiments in which one or more features or aspects of a described embodiment could be eliminated. Accordingly, it should be understood that the invention is not necessarily limited to any particular embodiment represented in the drawings or described herein, and that the purpose of the above detailed description and the phraseology and terminology employed therein is to describe the particular embodiment represented in the drawings, as well as investigations relating to the particular embodiment, and not necessarily to serve as limitations to the scope of the invention. Therefore, the scope of the invention is to be limited only by the following claims.

The invention claimed is:

1. A process comprising biologically producing hydrogen gas from organic waste by anaerobic fermentation of the organic waste with at least one strain of yeast, wherein the anaerobic fermentation is performed at a pressure maintained above atmospheric pressure and not greater than 12 Pa above atmospheric pressure, at an oxygen level maintained at less than 0.25%, at an elevated temperature maintained at 32° C. to 42° C., and at a pH maintained at 5.5 to 5.9, such that production of the hydrogen gas exceeds production of carbon dioxide over a period of twenty-four hours.

2. The process of claim 1, wherein the anaerobic fermentation is performed in a reactor tank.

3. The process of claim 1, further comprising:

adding a first amount of hydrogen-producing yeast to the organic waste before fermentation begins; and adding a second amount of hydrogen-producing yeast to the organic waste in the reactor tank after the start of fermentation and before peak production of hydrogen gas occurs.

4. The process of claim 3, further comprising decreasing latency of the anaerobic fermentation by adjusting an initial pH of the organic waste to approximately 6.0.

5. The process of claim 1, wherein the elevated temperature is about 37° C.

6. The process of claim 1, the process further comprising increasing iron ions in the organic waste to increase productivity of the hydrogen gas.

7. The process of claim 6, wherein increasing the iron ions comprises initially adding ferrous sulphate to the organic waste.

8. The process of claim 1, wherein the pH is 5.7.

9. The process of claim 1, wherein the pH is controlled by additions of acids and bases to the organic waste.

10. The process of claim 1, further comprising agitating the organic waste during the anaerobic fermentation.

11. The process of claim 1, wherein the anaerobic fermentation is performed on a mixture comprising the organic waste and water.

12. The process of claim 11, further comprising agitating the mixture during the anaerobic fermentation.

13. The process of claim 1, wherein the yeast is at least one yeast used in ethanol and/or wine production.

14. The process of claim 1, wherein the yeast is at least one of *Saccharomyces cerevisiae* and species of the genus *Schizosaccharomyces*.

15. The process of claim 1, wherein the anaerobic fermentation is performed without external additions of bacteria to the organic waste.

16. The process of claim 1, wherein the anaerobic fermentation is performed with external additions of bacteria to the organic waste.

17. The process of claim 1, wherein the organic waste is food waste.

* * * * *